United States Patent [19]

Leverett et al.

[11] Patent Number: 5,049,241
[45] Date of Patent: Sep. 17, 1991

[54] EXTRACTIVE DISTILLATION

[75] Inventors: Glenn F. Leverett, Vienna, W. Va.; Jan Wit, Werkendam, Netherlands

[73] Assignee: E. I. du Pont de Nemours and Company, Wilmington, Del.

[21] Appl. No.: 500,259

[22] Filed: Mar. 27, 1990

[51] Int. Cl.$^5$ ............................................... B01D 3/40
[52] U.S. Cl. ...................................... 203/67; 203/84; 570/178
[58] Field of Search ............................ 203/67, 57, 84; 570/178

[56] References Cited

U.S. PATENT DOCUMENTS

| | | | |
|---|---|---|---|
| 3,152,051 | 10/1964 | Fainberg et al. | 570/178 |
| 3,282,801 | 11/1966 | Wiist | 570/178 |
| 3,834,996 | 9/1974 | Aiso et al. | 570/178 |
| 4,558,167 | 12/1985 | Reigel et al. | 203/67 |
| 4,898,645 | 2/1990 | Voigt et al. | 203/67 |

FOREIGN PATENT DOCUMENTS

| | | | |
|---|---|---|---|
| 0645110 | 7/1962 | Canada | 203/67 |
| 0886714 | 1/1962 | United Kingdom | 570/178 |

Primary Examiner—Virginia Manoharan

[57] ABSTRACT

Process of separating hydrogen chloride and tetrafluoroethylene by extractively distilling a mixture thereof in the presence of an extractant that substantially alters the relative volatilities of the hydrogen chloride and the tetrafluoroethylene, for example, a perhalogenated organic extractant, such as perfluorocyclobutane, hexafluoropropylene or 1,1,2-trifluoro-1,2,2-trichloroethane.

13 Claims, No Drawings

EXTRACTIVE DISTILLATION

BACKGROUND OF THE INVENTION

1. Field of the Invention

This invention relates to the use of selected extractive distillation agents to separate tetrafluoroethylene (TFE) and hydrogen chloride (HCl).

2. Background

Tetrafluoroethylene can be made by the dehydrochlorination o Generally, it is made by the pyrolysis of chlorodifluoromethane ($CF_2HCl$). Ideally, two moles of $CF_2HCl$ form one mole of TFE and two moles of HCl. Sometimes steam is used as a diluent in the pyrolysis, but this leads to problems, such as equipment corrosion and the formation of undesirable by-products (see U.S. Pat. No. 4,849,554). The HCl recovered is contaminated with water and high-boiling fluorocarbons. Aqueous HCl is of considerably less value than anhydrous HCl, which can be used in various chemical reactions Another process disclosed in the aforesaid patent uses $CO_2$ as a diluent, but experiments have which causes contamination of the waste HCl with HF when the HCl is separated from the TFE by scrubbing with water.

Other known processes for the pyrolysis of $CF_2HCl$ are also anhydrous, and may use recycle gases as diluents. In such processes, TFE is separated from unconverted reactant and from by-products by distillation, and is recovered as its HCl azeotrope. This is desirable in that the azeotrope is much less explosive than pure TFE, and can be stored and handled with greater safety. Before use for polymerization, however, it is necessary to separate the TFE from HCl, and this is usually done by scrubbing with water to make dilute waste aqueous HCl, then with caustic to remove traces of HCl, and then with cold glycol to remove most of the water. The monomer is then dried, inhibited, compressed, stripped to remove low boilers, and finally refined to remove inhibitor and other high boilers. This is a complex process, requiring extensive equipment, and produces aqueous HCl of little value as a by-product.

It would be desirable to find a way to separate TFE from HCl in the $CF_2HCl$ pyrolysis crude product without diluting the HCl with water.

At normal processing conditions of pressure and temperature, the azeotrope composition is approximately 67 mole percent HCl and 33 mole percent TFE. The composition of the azeotrope changes very little with temperature and pressure. Therefore, breaking the azeotrope by operating at extremely low or high pressure cannot be accomplished.

SUMMARY OF THE INVENTION

In its broadest sense, the invention resides in a process of separating HCl and TFE by extractively distilling through an extractive distillation column a mixture thereof in the presence of an extractant that substantially alters the relative volatilities of the HCl and the TFE. Various embodiments of the invention include processes wherein the extractant is an organic compound; wherein the liquid organic compound is a perhalogenated compound; wherein the halogens of the perhalogenated compound are selected from fluorine and chlorine; and wherein there are recovered an overhead fraction consisting substantially of HCl and a bottom fraction consisting substantially of TFE and extractant. Other embodiments will become apparent hereinafter, and it is to be understood that there is no intent to limit the invention to specific embodiments.

DETAILED DISCLOSURE OF THE INVENTION

Distillation of mixtures containing HCl and TFE results in the isolation of their azeotrope, which contains 1 about 67 mole percent HCl and boils at $-92°$ C. at atmospheric pressure. Distillation of this azeotrope or other mixtures of HCl and TFE in the extractive distillation process of the present invention separates the two materials. In a preferred embodiment the TFE goes down the column with the extractant, from which it can be separated by distillation, with the extractant available for recycle to the extractive distillation step, and the HCl goes overhead in the extractive distillation column and can be used as anhydrous HCl or scrubbed out to make concentrated HCl. The mixture of TFE and extractant can be stored with greater safety than pure TFE.

In the aforesaid preferred embodiment the bottom product from the extractive distillation column, which contains substantially TFE and extractant, can be sent to a second distillation column wherein the TFE is taken off overhead and the extractant is taken off as the bottom product. This bottom product can be recycled to the upper section of the extractive distillation column. Depending on the purity of the feed stream entering the extractive distillation column, it may be desirable to purify all or a portion of the extractant before it is recycled to the extractive distillation column.

The ease of separation of two components by distillation depends on the "relative volatility" of the two components, which is defined by the well known equation as (for HCl and TFE in this case):

$$\text{alpha (HCl/TFE)} = (Y\ HCl/X\ HCl)(X\ TFE/Y\ TFE)$$

where Y HCl and X HCl are the mole fractions of HCl in the vapor phase and the liquid phase, respectively, at equilibrium, and Y TFE and X TFE are the mole fractions of TFE in the vapor phase and liquid phase, respectively, at equilibrium. Robinson, C. S. and Gilliland, E. R., "Elements of Fractional Distillation," 4th ed, 1950, McGraw-Hill Book Co., Inc. In the case of the azeotrope, alpha = 1. For the separation to be carried out in a practical way, the value of alpha (HCl/TFE) should be at least 1.3. The function of the extractant in this invention is to increase the value of alpha to at least 1.3. Also, for the separation to be practical, the extractant must be easily separated form the TFE/extractant mixture. This means that the value of alpha (TFE/extractant) must also be at least 1.3.

The requirements of the extractant, in addition to providing the desired alpha (HCl/TFE) of at least 1.3, are that it be non-reactive with the other components in the system, that it be substantially free of chain transfer activity in the polymerization of TFE, and that it be thermally stable under process conditions.

The extractant preferably has a boiling point sufficiently higher than TFE, such that the separation of TFE from the extractant can be easily accomplished. For example, there are, in fact, no organic compounds, fully halogenated with fluorine and/or chlorine, which have atmospheric boiling points between TFE ($-76°$ C.) and $-40°$ C. Therefore, in such embodiments, the selection of pure extractant is limited to those having atmospheric pressure boiling points of at least −40° C. However, the use of mixtures of extractants may be desirable in some cases.

As illustrated by the examples, the relative volatility of HCl/TFE decreases as the concentration of the extractant in the liquid phase decreases. Thus, some minimum concentration of extractant must be maintained in order to obtain the desired separation. If the boiling point of the extractant is too high, the necessary extractant concentration can only be maintained by using a very high extractant feed flow, which will increase the size of the extraction column required and give a more dilute concentration of TFE in the bottom product. This, in turn, requires a larger diameter column for the separation of the TFE from the extractant. For practical considerations the maximum atmospheric boiling points of the extractant should be about 60° C., although operation above 60° C. might be feasible if the particular extractant resulted in a very high value of the relative volatility of HCl to TFE at very low extractant concentrations.

The effect of an extractant on the relative volatility of HCl/TFE can be readily determined by charging the components HCl and TFE plus the extractant to a conventional equilibrium cell at a controlled temperature and measuring the composition of the liquid and vapor phases. Generally, the value of alpha (HCl/TFE) will vary with the concentration of the extractant in the liquid phase.

In another preferred embodiment the extractant can be a perhalogenated organic extractant in which the halogens are selected from the class consisting of fluorine and chlorine, preferably fluorine, and the extractant preferably has an atmospheric pressure boiling point of −40° C. to 60° C. Preferably, the extractant is used in a quantity such that at least 20 mole percent concentration of the extractant is maintained in the liquid phase. Suitable preferred extractants include the cyclic dimer of tetrafluoroethylene, that is, perfluorocyclobutane ($C_4F_8$), hexafluoropropylene (HFP; $C_3F_6$), and $CF_2Cl$-$CFCl_2$, that is, 1,1,2-trifluoro-1,2,2-trichloroethane ($C_2F_3Cl_3$).

EXAMPLE 1

Table I is representative of vapor-liquid equilibrium measurements for the system TFE/HCl/$C_4F_8$; the boiling point of $C_4F_8$ is −6° C. at atmospheric pressure.

TABLE I

| Temp., °C. | Mole % in the Liquid | | | alpha (HCl/TFE) | alpha (TFE/$C_4F_8$) |
|---|---|---|---|---|---|
| | $C_4F_8$ | HCl | TFE | | |
| −10 | 64.8 | 28.1 | 7.1 | 2.84 | 9.2 |
| −10 | 40.8 | 44.0 | 15.2 | 2.23 | 8.1 |
| −10 | 13.6 | 53.0 | 33.4 | 1.70 | 6.5 |
| −20 | 58.6 | 19.0 | 22.4 | 3.96 | 11.1 |
| −20 | 29.9 | 39.2 | 30.9 | 2.53 | 8.5 |
| −20 | 13.5 | 54.1 | 32.4 | 1.45 | 8.2 |
| −30 | 63.8 | 29.1 | 7.1 | 3.14 | 13.7 |
| −30 | 41.9 | 6.4 | 51.7 | 3.82 | 7.5 |
| −30 | 38.0 | 47.4 | 14.6 | 1.99 | 10.5 |
| −30 | 31.5 | 41.6 | 26.9 | 2.39 | 7.4 |
| −30 | 12.7 | 54.2 | 33.1 | 1.63 | 8.3 |

Table I shows that the value of alpha (HCl/TFE) is well above 1.3 in the presence of $C_4F_8$ even at $C_4F_8$ concentrations as low as 12.7 mole percent in the liquid phase. Furthermore, the value of alpha (TFE/$C_4F_8$) is well above 1.3. Therefore the TFE is easily separated from the extractant, $C_4F_8$.

EXAMPLE 2

Table II is representative of vapor-liquid equilibrium measurements for the system TFE-HCl-$C_3F_6$ at −20° C. The boiling point of $C_3F_6$ at atmospheric pressure is −29.4 C.

TABLE II

| Mole % in Liquid Phase | | | alpha (HCl/TFE) | alpha (TFE/$C_3F_6$) |
|---|---|---|---|---|
| $C_3F_6$ | HCl | TFE | | |
| 69.7 | 20.3 | 10.0 | 2.6 | 4.2 |
| 59.6 | 27.1 | 13.3 | 2.4 | 4.2 |
| 50.2 | 33.4 | 16.4 | 1.9 | 4.2 |
| 39.5 | 40.5 | 20.0 | 1.5 | 4.2 |

Table II shows that the value of alpha (HCl/TFE) above 1.3 in the presence of $C_3F_6$ at $C_3F_6$ concentrations as low as 40 mole percent in the liquid phase. Furthermore, the value of alpha (TFE/$C_3F_6$) is well above 1.3. Therefore, TFE is easily separated from the extractant, $C_3F_6$.

EXAMPLE 3

Table III is representative of vapor-liquid equilibrium measurements for the system TFE-HCl-$C_2F_3Cl_3$ at −25° C. $C_2F_3C_{13}$ boils at 47.6° C. at atmospheric pressure:

TABLE III

| Mole % in Liquid Phase | | | alpha (HCl/TFE) | alpha (TFE/$C_2F_3Cl_3$) |
|---|---|---|---|---|
| $C_2F_3Cl_3$ | HCl | TFE | | |
| 69.3 | 20.6 | 10.1 | 2.5 | 200 |
| 59.1 | 27.4 | 13.5 | 2.1 | 200 |
| 51.0 | 32.8 | 16.2 | 1.8 | 200 |
| 38.7 | 41.1 | 20.2 | 1.4 | 200 |

Table III shows that the value of alpha (HCl/TFE) is above 1.3 in the presence of $C_2F_3Cl_3$ at $C_2F_3Cl_3$ concentrations as low as 40 mole percent in the liquid phase. Furthermore, the value of alpha (TFE/$C_2F_3Cl_3$) is well above 1.3. Therefore, TFE is easily separated from the extractant, $C_2F_3Cl_3$.

The information presented in the above examples can be easily applied to design the extractive distillation column and the extractant removal column by using well-established engineering principles. Although the relative volatility data of the examples provide embodiments of specific halogenated compounds of the invention, other halogenated compounds and their mixtures could be employed as suitable extractants in the examples.

What is claimed is:

1. Process of separating hydrogen chloride and tetrafluoroethylene by extractively distilling through an extractive distillation column a mixture thereof in the presence of an extractant that substantially alters the relative volatilities of the hydrogen chloride and the tetrafluoroethylene, and recovering an overhead fraction consisting essentially of hydrogen chloride and a bottom fraction consisting essentially of tetrafluoroethylene and the extractant.

2. Process of claim 1 wherein the extractant is an organic compound.

3. Process of claim 2 wherein the extractant is a perhalogenated organic compound wherein the halogens are selected from a group consisting of fluorine and chlorine.

4. Process of claim 3 wherein the tetrafluoroethylene and extractant are separated and the recovered extractant is recycled to the extractive distillation column.

5. Process of claim 4 wherein the tetrafluoroethylene and extractant are separated by distillation.

6. The process of claim 3 wherein the extractant has an atmospheric pressure boiling point of −40° C. to 60° C., the extractant concentration in the liquid phase is at least 20 mole percent, and the recovered extractant is returned to the extractive distillation column.

7. The process of claim 3 wherein the mixture is the product of the dehydrochlorination of chlorodifluoromethane.

8. The process of claim 3 wherein the mixture is an azeotrope of tetrafluoroethylene and hydrogen chloride.

9. The process of claim 3 wherein the extractant is selected from a group consisting of perfluorocyclobutane, hexafluoropropylene, and 1,1,2-trifluoro-1,2,2-trichloroethane.

10. The process of claim 3 wherein the extractant is perfluorinated.

11. The process of claim 9 wherein the extractant is perfluorocyclobutane.

12. The process of claim 9 wherein the extractant is hexafluoropropylene.

13. The process of claim 9 wherein the extractant is 1,1,2-trifluoro-1,2,2-trichlorethane.

* * * * *

UNITED STATES PATENT AND TRADEMARK OFFICE
CERTIFICATE OF CORRECTION

PATENT NO. : 5,049,241

DATED : September 17, 1991

INVENTOR(S) : Leverett et al

It is certified that error appears in the above-identified patent and that said Letters Patent is hereby corrected as shown below:

Column 1, line 11, after "chlorination" delete "0" and insert -- of $CF_2HCl$ --.

Column 1, line 23, after "have" insert -- shown that this leads to the formation of some $COF_2$, --.

Column 2, line 8, delete "1".

Signed and Sealed this

Thirtieth Day of March, 1993

Attest:

STEPHEN G. KUNIN

*Attesting Officer*      *Acting Commissioner of Patents and Trademarks*